United States Patent [19]
Ramsey, III

[11] Patent Number: 6,148,222
[45] Date of Patent: Nov. 14, 2000

[54] ESOPHAGEAL CATHETERS AND METHOD OF USE

[75] Inventor: Maynard Ramsey, III, Tampa, Fla.

[73] Assignee: CardioCommand, Inc., Tampa, Fla.

[21] Appl. No.: 09/113,873

[22] Filed: Jul. 10, 1998

[51] Int. Cl.[7] .................................................. A61B 5/04
[52] U.S. Cl. ...................... 600/380; 600/373; 604/101; 604/102; 607/116
[58] Field of Search .......................... 600/372, 373–381, 600/509; 607/116, 133; 604/22, 101, 102, 11

[56] References Cited

U.S. PATENT DOCUMENTS

| | | |
|---|---|---|
| 4,423,725 | 1/1984 | Baran et al. . |
| 4,573,966 | 3/1986 | Weikl et al. . |
| 4,581,017 | 4/1986 | Sahota . |
| 4,610,662 | 9/1986 | Weikl et al. . |
| 4,824,436 | 4/1989 | Wolinsky . |
| 5,087,244 | 2/1992 | Wolinsky et al. . |
| 5,135,474 | 8/1992 | Swan et al. . |
| 5,222,941 | 6/1993 | Don Michael . |
| 5,256,141 | 10/1993 | Gencheff et al. ........................ 604/101 |
| 5,328,470 | 7/1994 | Nabel et al. . |
| 5,415,636 | 5/1995 | Forman . |
| 5,588,961 | 12/1996 | Leone et al. .............................. 604/96 |
| 5,674,198 | 10/1997 | Leone . |
| 5,846,218 | 12/1998 | Brisken et al. ........................... 604/96 |

*Primary Examiner*—Linda C. M. Dvorak
*Assistant Examiner*—David Ruddy
*Attorney, Agent, or Firm*—Gerstman, Ellis & McMillin, Ltd.

[57] ABSTRACT

A method and a catheter for passing a therapeutic electric current to, or sensing electric signals from, the body of a patient. The catheter is inserted into the esophagus of the patient, temporarily sealing a space surrounding a portion of the catheter containing one or more electrodes within the esophagus wall. The space is filled with an electrically conductive liquid (electrolyte). Then, an electric current is passed through electrodes to the conductive liquid between the esophagus wall and an electrode carried on the catheter in spaced relation from the esophagus wall or to other electrodes in the heart or body surface.

18 Claims, 2 Drawing Sheets

ESOPHAGEAL CATHETERS AND METHOD OF USE

FIELD OF THE INVENTION

The present invention concerns novel esophageal catheters and methods of using esophageal catheters.

BACKGROUND OF THE INVENTION

It has been found that cardiac monitoring, pacing, cardioversion and defibrillation can be performed using electrodes carried on catheters placed within the esophagus. Esophageal catheters are often preferred because they are less expensive, less risky, much easier and faster than surgical methods or other methods of placing electrodes close to or on the heart. Esophageal catheters are more direct, more sensitive, and often easier than methods involving the use of external electrodes. Thus, esophageal catheters can be advantageously used in emergency situations or temporary situations such as during surgery.

When using esophageal catheters, it is necessary to get good electrical conductivity between electrodes carried on the catheters and the wall of the esophagus. It is presently typical to place the electrode directly against the wall of the esophagus. One problem with doing so is the potential for current burns to occur at the point of contact between the electrode and the esophagus wall, especially when performing defibrillation.

The problem of current burn can be reduced or eliminated by using an electrode with a large surface area. However, a large electrode is more difficult to insert into the esophagus, and it is not convenient.

I have invented a novel type of esophageal catheter, which reduces or eliminates the potential for catheter burn, and which can be made small and thin for easy, quick and convenient use.

An object of the present invention is to provide an esophageal catheter useful in cardiac monitoring, pacing, cardioversion and/or defibrillation with reduced risk of current burn, and which has a small outer diameter.

Another object is to provide an improved esophageal catheter that is easy and economical to construct and is simple and convenient to use.

Other objects and advantages of the present invention will become apparent as the description proceeds.

SUMMARY OF THE INVENTION

In accordance with the present invention, an esophageal catheter is provided having a generally elongated tubular member, a first balloon located in a distal portion of the catheter, one or more additional balloons located proximally of the first balloon, one or more electrodes, and one or more access ports in the catheter sidewall. The balloons are connected by one or more lumens to a proximal portion of the catheter. The electrodes are connected by wire to the proximal portion of the balloons. The access ports are also connected by one or more lumens to the proximal portion of the catheter. The electrodes and access ports are positioned in relation to the balloons so that there is at least one electrode and one access port between a pair of balloons.

In use, the catheter is inserted into the esophagus. Once properly positioned within the esophagus, preferably the most distal balloon and one or more of the proximally located balloons are inflated to create one or more chambers outside of the catheter and within the esophagus. A conductive liquid (an electrolyte) is injected into the chamber or chambers through one or more access ports, creating an electrical connection between the wall of the esophagus and at least one electrode. The catheter may then be used to monitor the electrical activity of the heart and for cardiac pacing, cardioversion or defibrillation.

Specifically, a therapeutic electric current for such monitoring of heart activity, cardiac pacing, cardioversion, or defibrillation is applied by the following method which comprises the following steps:

(a) inserting a catheter into the esophagus of the patient;

(b) temporarily sealing a space surrounding a portion of the catheter within the esophagus wall;

(c) filling the space with an electrically conductive liquid, for example, saline or sodium bicarbonate solution, while assuring that essentially all air is removed from the space; and (d) passing an electric current through the conductive liquid between the esophagus wall and an electrode carried on the catheter in spaced relation with the esophagus wall. Typically the current passes to one or more other electrodes present in the esophagus, or to electrodes in the heart or other body surface or organ.

Because of the spaced relation of the electrode from the esophagus wall, the electric current must pass through the conductive liquid. The effect of this is to reduce or completely eliminate the problem of current burn of the esophagus, even though a small electrode is used, and even under conditions of high current flow and higher voltage, as may be found with a defibrillation or cardioversion procedure. Nevertheless, the electrical connection that is defined between an electrode on the catheter and the esophagus wall by the addition of the conductive liquid can be very sensitive for the effective monitoring of electrical signals from the heart, and also effectively carries larger current flows. Preferably, the minimum spacing between the electrode and the esophagus wall is at least 2 mm.

An advantage is provided in that electric currents emanating off of a small surface electrode can spread in the electrolyte, and thus reduce the current density while passing through the liquid, to be received by an area of the esophagus that is larger than the area of the electrode.

The electric current can originate in a power source outside of the patient, being passed to the electrode by a conductor within the catheter, and from there to the patient through the electrolyte. The electric current can also originate in the patient (such as the heart) and passes from the patient through the electrolyte to the electrode, and from there to a sensor outside of the patient.

A more detailed explanation of the invention is provided in the following description and claims, and is illustrated in the accompanying drawings.

DETAILED DESCRIPTION OF THE ILLUSTRATIVE EMBODIMENTS

Figure 1:
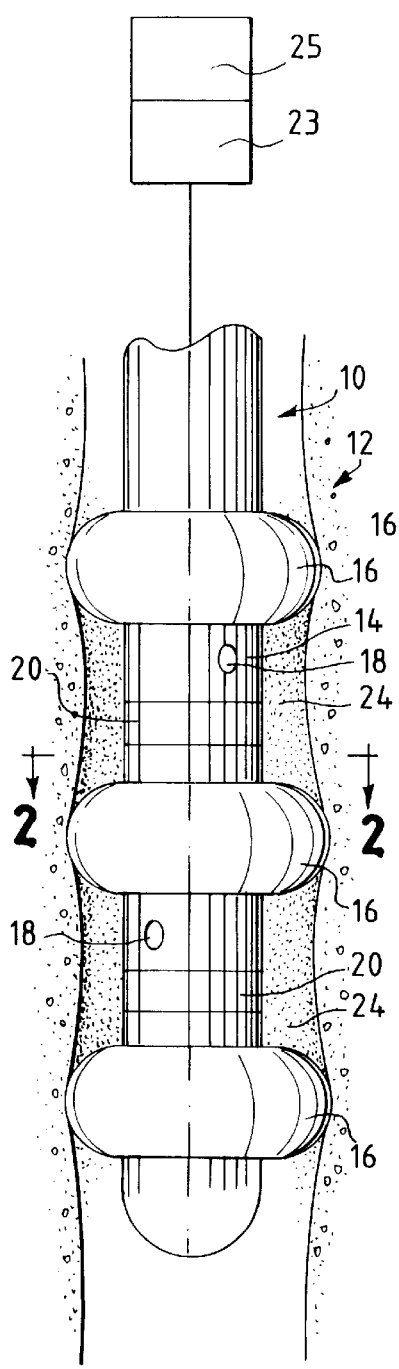
FIG. 1 is a partly diagrammatic illustration of a catheter constructed in accordance with the principles of the present invention, showing its balloons in inflated condition.
Figure 2:
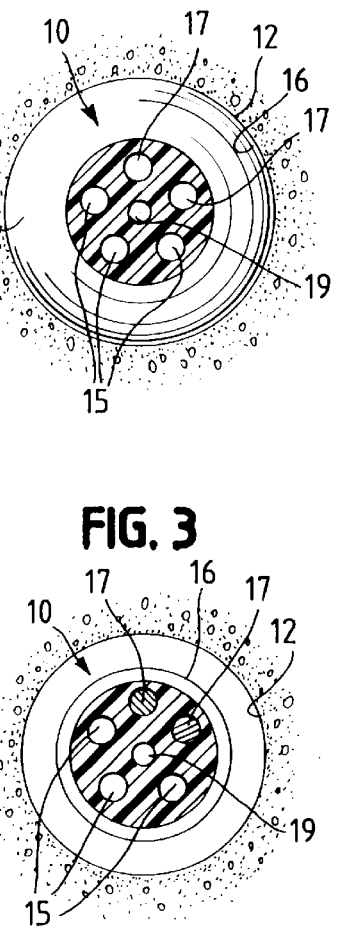
FIG. 2 is a cross-section of the catheter with an inflated balloon of FIG. 1, taken along line 2—2 of FIG. 1.
Figure 3:
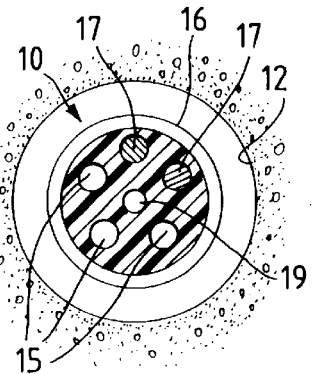
FIG. 3 is a cross-section similar to FIG. 2 except that the balloon is deflated.
Figure 4:
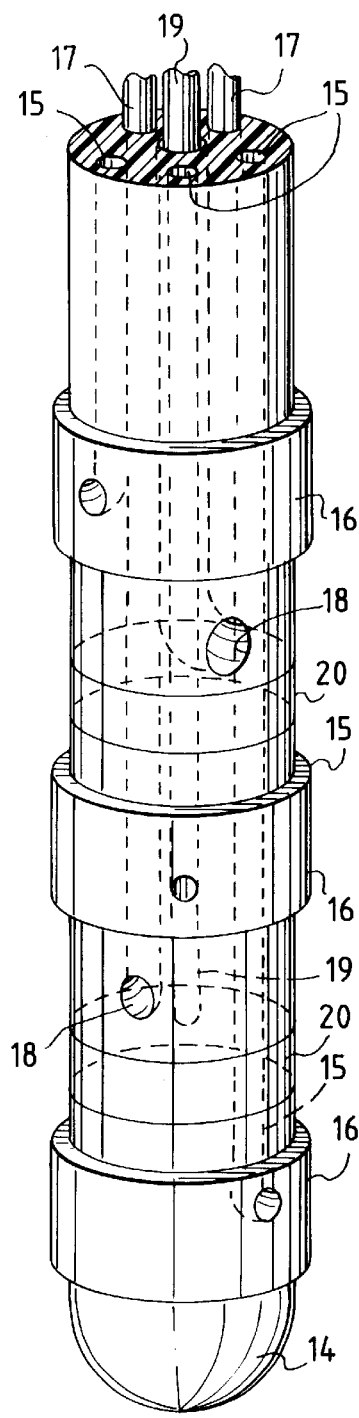
FIG. 4 is a perspective view of the distal end portion of the catheter of FIG. 1.
Figure 5:
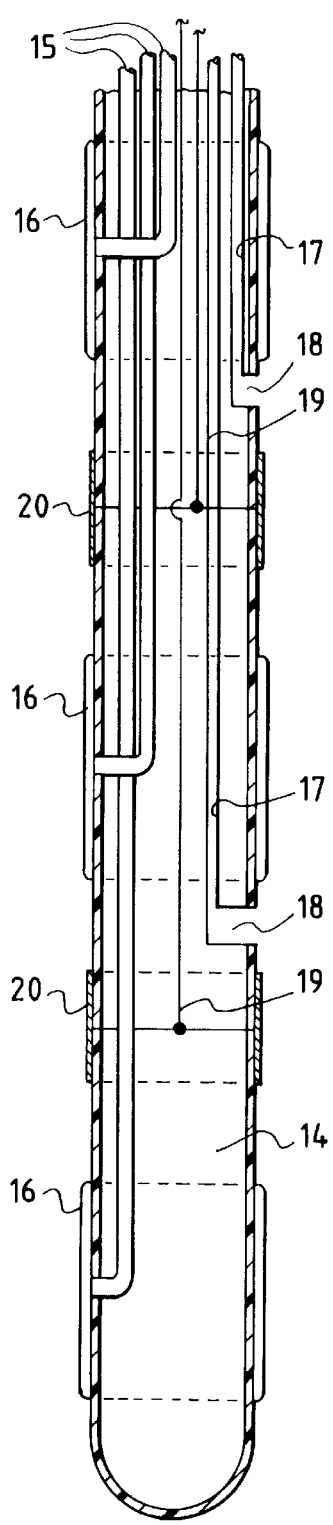
FIG. 5 is a longitudinal section of the catheter of FIGS. 1–4.

Referring to FIG. 1, a generally elongated tubular catheter 10 is illustrated. The catheter 10 is shown within a tubular passage 12 representing the esophagus. The catheter comprises a relatively thin catheter body 14, which extends between and through balloons 16 and carries them. Balloons 16 connect to conventional inflation lumens 15 (FIG. 4). Although illustrated with a drawing showing three balloons, the catheter could include any number of balloons of at least two.

As is conventional, catheter body 14 can extend proximally outside the body of the patient to connect at its proximal end to equipment 23 for balloon inflation and for electrolyte injection through ports 18. The catheter also may connect to electrically powered equipment 25 for cardiac monitoring, pacing, cardioversion and/or defibrillation. Catheter body 14 may be constructed of materials sufficiently flexible so as to be able to follow and conform to the natural shape of the esophagus, but sufficiently stiff to hold its generally linear shape while being pushed into the esophagus.

Positioned between the balloons on the tubular member are one or more catheter lumens 17 (FIG. 4) terminating in electrolyte ports 18, and one or more electrodes 20 connected through the catheter proximal end by conductors 19 within the catheter, as is conventional. Electrolyte ports 18 are used to sequentially inject and remove an electrically conductive fluid into closed space 24 between esophagus wall 12 and catheter 10.

Generally, the catheter of this invention can be made by conventional means, and may use generally conventional structure for the respective balloons 16, electrolyte ports 18, electrodes 20, the connecting lumens and conductors 15, 17, 19, all formed in a typically extruded catheter body 14.

The catheter of this invention may be used to pass a therapeutic electric current to, or to sense electric signals from, the body of a patient in the following manner:

The catheter 10 may be conventionally inserted into the esophagus of the patient through the nose or mouth, followed by temporarily sealing a space 24 surrounding a portion of the catheter within the esophagus wall by inflating at least two of the balloons 16 by providing pressurized liquid or air to the balloons through the respective connected lumens 15. Spaces 24, as shown in FIG. 1, are defined between the walls 12 of the esophagus on the outside, the catheter body 14 on the inside, and respective inflated balloons 16 at the ends, to provide one or more of the sealed spaces 24. Each sealed space 24 communicates with an electrolyte port 18 and with an electrode 20. If desired, the central balloon 16 may be deflated, or even omitted, so that sealed space 24 communicates with a pair of electrolyte ports 18, so that fluid may be simultaneously inserted and removed from the space to clear out air, to prevent over pressurization, and/or to remove the electrolyte after use. Thus the esophagus does not become over-inflated, and all electrolyte may be flushed away, if desired, and replaced with pure water, for example. Thus electrolytes may be used which are best removed from the patient after use.

The sealed space 24 is filled with an electrically conductive liquid such as a mildly hypertonic saline solution or the like, for example, 2% saline solution. Thus, an electrical connection between the wall 12 of the esophagus and each electrode 20 results, across which a therapeutic electric current may be passed, or across which electric signals may be sent to the electrode or electrodes 20 from the body of the patient. For example, heart action may be monitored through one or both electrodes 20 in monopolar or bipolar fashion, with electrical impulses from the heart being thus monitored and the resulting signal passing from electrode or electrodes 20 to electronic sensing equipment 25 via conductors 19.

Alternatively, heartpacing, cardioversion, and/or defibrillation may be accomplished by the generation of appropriate electric pulses or signals from electronic equipment 25, which pulses or signal pass along conductor or conductors 19 to the respective electrode or electrodes 20. From there, the pulse or signal is conveyed across the conductive liquid 24 to the esophagus. with greatly reduced risk of burning of the esophagus wall, and with essentially no concern about obtaining a proper electrical connection between electrode 20 and the esophagus wall 12, since the electrical connection is naturally and spontaneously provided by the conductive liquid without any physical connection between an electrode and the esophagus wall.

Upon termination of the therapeutic procedure, the conductive liquid 24 can be removed if desired from the esophagus through electrolyte ports 18 and their connected flow lumens 17; balloons 16 may be deflated; and the catheter is withdrawn.

The procedure of this invention can be performed very rapidly for emergency use if desired, while a strong signal or electrical impulse can be provided in either direction across the electrolyte bridge between electrode 20 and the esophagus wall. This can be done without the known problems of driving an electrical signal or impulse through the skin without burning, and is performed at a location which is quite near to the heart and not separated from the heart by the ribs. This technique may be also used to pass current from the skin to the esophagus if needed. Also, the catheter of this invention can be reused on the same patient, if needed or desired, shortly after the first use, even though the catheter may be of a disposable type.

Figure 6:
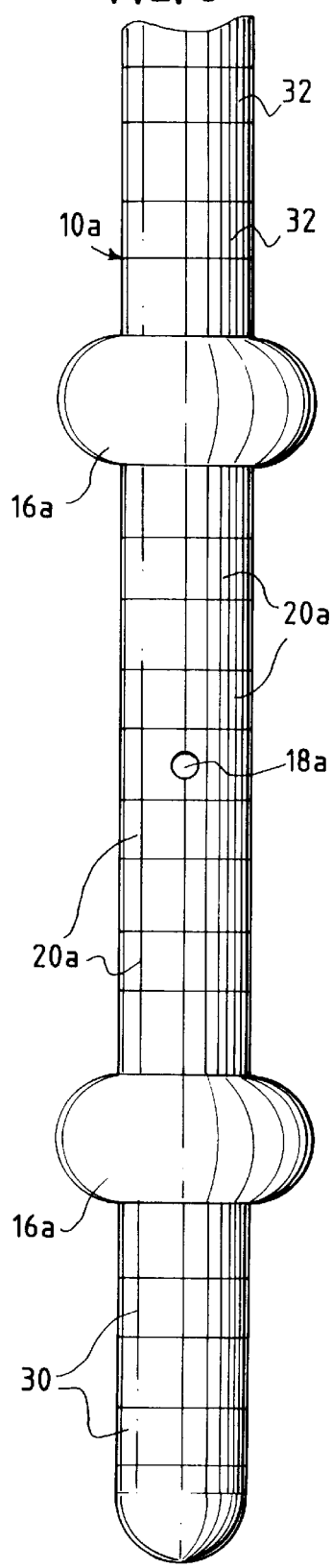
FIGS. 6 and 7 are enlarged plan views of the distal end portions of other embodiments of balloon catheters in accordance with this invention.

Referring to FIG. 6, another embodiment of catheter of this invention is disclosed, similar in structure and function to the previously described catheter except as otherwise indicated herein. Catheter 10*a* carries a pair of balloons 16*a* which are similar to the catheter balloons of the previous embodiment, being similarly connected to inflation lumens within the catheter, as is conventional.

By way of difference, catheter 10*a* carries four, or any desired plural number, cardioversion electrodes 20*a*, each of which is connected to a conductor extending through the catheter as in the previous embodiment for connection to electrically powered equipment 25 for cardiac monitoring, pacing, cardioversion, and/or defibrillation, as in the previous embodiment.

Also, catheter 10*a* carries added electrodes 30 distal to both balloons 16*a*, which electrodes may be of a design similar to that described in the previous embodiment, although differently placed along catheter 18, being also connected to electrode conductors within the catheter. Electrodes 30 may be used for ventricular pacing after a cardioversion procedure has taken place, being separately controlled through conductors which are separate from the conductors that connect to electrodes 20*a*.

Fluid access port 18*a*, between balloons 16*a*, communicates with a lumen in a manner similar to port 18 of the previous embodiment, for similar purposes.

Additional electrodes 32 may be carried by catheter 10a at a position proximal of catheter balloons 16a, these electrodes being optional, and used for sensing, for example.

Figure 7:
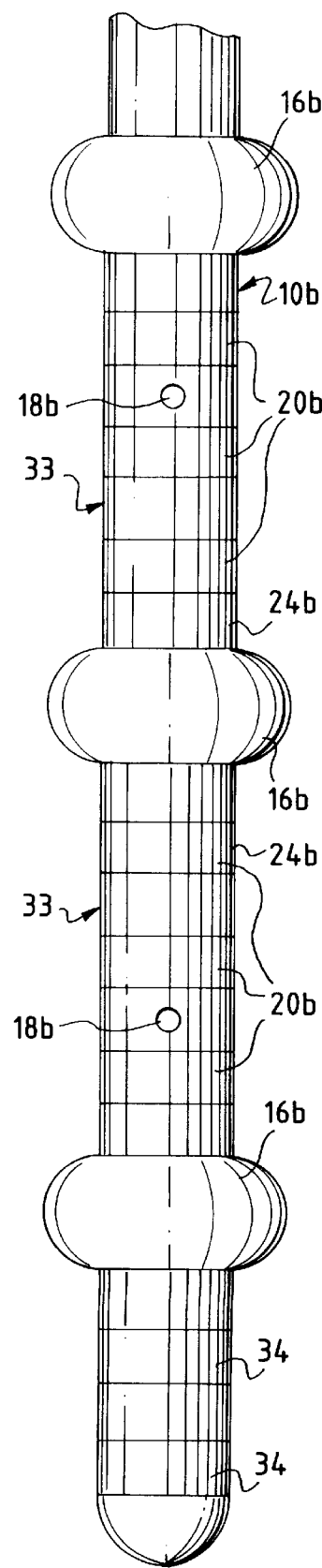

Referring to FIG. 7, another alternate design of catheter is shown, for use in accordance with this invention. Here also, catheter 10b is similar in structure and in function to the catheters of the previous embodiments, except as otherwise indicated herein.

Catheter 10b carries three balloons 16b, each being connected by inflation lumens to the proximal end of the catheter in conventional manner.

In this embodiment, each of the catheter portions 33 between the respective balloons 16b carry three, or any plural number, of ring electrodes 20b, which are respectively connected by a conductor or plural conductors to the proximal catheter end as in previous embodiments, for electrical communication with electrically powered equipment similar to equipment 25. As in FIG. 6, these electrodes may be used for cardioversion. Electrolyte fluid may pass into the spaces 24b between balloons 16b through ports 18b, which communicate with lumens extending through the catheter in a manner similar to lumens 17 of the embodiment of FIGS. 1–5, so that the catheter of FIG. 7 (and FIG. 6) may be used in the manner previously described.

As in the embodiment of FIG. 6, catheter 10b also carries a pair of ventricular pacing electrodes 34 at a position distal to the balloons 16b, which electrodes are conventionally connected to conductors leading to the proximal end of the catheter.

Although illustrative embodiments of the invention have been shown and described, it is to be understood that various modifications and substitutions may be made by those skilled in the art without departing from the spirit and scope of the present invention.

That which is claimed:

1. The method of passing a therapeutic electric current to, or sensing electric signals from, the body of a patient, which comprises:

(a) inserting a catheter into the esophagus of the patient;
   (b) temporarily sealing a space surrounding a portion of said catheter within the esophagus wall;
   (c) filling the space with an electrically conductive liquid; and
   (d) passing an electric current through said conductive liquid between the esophagus wall and an electrode carried on said catheter in spaced relation from the esophagus wall.

2. The method of claim 1 in which said electric current passes from said electrode through the esophagus wall to at least one electrode within the interior of the heart.

3. The method of claim 1 in which said electric current passes from the electrode through the esophagus wall and through the outer surface of the body.

4. The method of claim 1, in which said electric current is passed for therapeutic monitoring or treatment of the heart of the patient.

5. The method of claim 4 in which said electric current originates in the heart and passes to a sensor through the electrode.

6. The method of claim 4 in which said electric current originates in a power source outside of said patient and passes to said electrode and the patient through the catheter.

7. An esophageal catheter comprising:

an elongated, tubular member having a proximal portion and a distal portion;

a first balloon located in the distal portion of said tubular member;

a second balloon located proximally of said first balloon on said tubular member;

said balloons being connected to at least one inflation lumen;

at least one first electrode located on said tubular member at a first space between said first and second balloons; and at least one first access port located on said tubular member at the first space between said first and second balloons; a first lumen in said elongated tubular member extending between said first access port and a proximal portion of said tubular member for passing conductive liquid to and from said first space outside of said catheter and between said balloons; a third balloon, spaced from said first and second balloons along said catheter, said third balloon and one of said first and second balloons defining a second space along and outside of said catheter, said second space communicating with at least one second electrode located on the catheter, each of said first and second electrodes communicating with a proximal portion of said catheter through a conductor, at least one second access port located on said tubular member at said second space; and a second lumen in said elongated tubular member extending between said second access port and a proximal portion of said tubular member for the further passing of conductive liquid to and from said second space.

8. The catheter of claim 7 in which each of said catheter spaces communicates with a plurality of spaced electrodes on said catheter, each of said plurality of electrodes also communicating with a proximal portion of said catheter through a conductor.

9. The catheter of claim 8 in which three electrodes occupy each space between the catheter balloons.

10. The catheter of claim 8 in which at least one added electrode is carried on said catheter at a position distal to said first and second balloons.

11. The catheter of claim 7 in which at least one added electrode is carried on said catheter at a position distal to said first and second balloons.

12. The catheter of claim 7 in which at least one added electrode is carried on said catheter at a position proximal to said first and second balloons.

13. The catheter of claim 7 in which added electrodes are carried on said catheter at positions distal and proximal to said first and second balloons.

14. An esophageal catheter sized to fit in the esophagus and comprising:

an elongated, tubular member having a proximal portion and a distal portion;

a first balloon located in the distal portion of said tubular member;

a second balloon located proximally of said first balloon on said tubular member;

said balloons being connected to at least one inflation lumen, and sized to seal against the esophagus;

at least one electrode located on said tubular member between said first and second balloons; and at least one access port located on said tubular member between said first and second balloons; and a lumen in said elongated tubular member extending between said access port and a proximal portion of said tubular member for passing conductive liquid to and from a space outside of said catheter and between said balloons; said electrode being unipolar.

15. The catheter of claim 14 in which a third balloon is present, spaced from said first and second balloons along said catheter, whereby said three balloons define two spaces along and outside of said catheters which are each respectively positioned between two of said balloons, each of said spaces communicating with an electrode on the catheter, each electrode communicating with a proximal portion of said catheter through a conductor, and apertures which communicate with at least one catheter lumen for the transfer of electrolyte liquid between said spaces and the proximal portion of said catheter.

16. The catheter of claim 15 in which each of said catheter spaces communicates with a plurality of spaced electrodes on said catheter, each of said plurality of electrodes also communicating with a proximal portion of said catheter through at least one conductor.

17. The catheter of claim 16 in which three electrodes occupy each space between the catheter balloons.

18. The catheter of claim 14 in which added ventricular pacing electrodes are carried on said catheter at at least one of positions proximal or distal to said first and second balloons.

\* \* \* \* \*